US00PP34560P2

(12) United States Plant Patent
Machata

(10) Patent No.: US PP34,560 P2
(45) Date of Patent: Sep. 13, 2022

(54) ***CITRUS* TREE NAMED 'NOAH'**

(50) Latin Name: ***Citrus sinensis* hybrid**
Varietal Denomination: Noah

(71) Applicant: ROLLING MEADOW RANCH GROVES LLC, Lake Wales, FL (US)

(72) Inventor: Matthew Machata, Lake Wales, FL (US)

(73) Assignee: ROLLING MEADOW RANCH GROVES LLC, Lake Wales, FL (US)

( * ) Notice: Subject to any disclaimer, the term of this patent is extended or adjusted under 35 U.S.C. 154(b) by 0 days.

(21) Appl. No.: 17/180,216

(22) Filed: Feb. 19, 2021

(51) Int. Cl.
*A01H 5/10* (2018.01)
*A01H 6/78* (2018.01)

(52) U.S. Cl.
USPC ..... Plt./202
CPC ..... *A01H 6/785* (2018.05); *A01H 5/10* (2013.01)

(58) Field of Classification Search
USPC ..... Plt./202
CPC ..... A01H 6/785
See application file for complete search history.

*Primary Examiner* — Anne Marie Grunberg
(74) *Attorney, Agent, or Firm* — Allen, Dyer et al.

(57) ABSTRACT

A new and distinct cultivar of *Citrus Sinensis* plant, "Noah", is disclosed that is characterized by its resistance or tolerance to *Citrus* greening, also known as *Huanglongbing*.

7 Drawing Sheets

Variety denomination: The present invention relates to a new and distinct cultivar of *Citrus Sinensis* botanically known as *Citrus Sinensis* hybrid, referred to by the name of "Noah".

BACKGROUND

The new cultivar is the result of a sport limb found on a *Valencia* orange tree located in a *Citrus* grove in Lake Wales, Fla. All trees in the Lake Wales grove were infected with *Citrus* greening, including the newly discovered cultivar. *Citrus* greening is a devastating bacterial disease caused by a gram negative, phloem limited bacteria called *Candidatus Liberibacter asiaticus* (CLas).

When a *Citrus* tree is infected with *Citrus* greening its vascular tissue is clogged and the mobility of nutrients and photosynthates is severely limited. This infection has many detrimental effects on *Citrus* trees causing root and shoot dieback, increased fruit drop, decreased fruit size, high acid fruit with low sugar content, sparse canopies, small leaves with significant leaf drop under minimal environmental stress, low vigor, and ultimately premature death. A telltale sign of *Citrus* greening infection is the leaves of a *Citrus* tree possessing a blotchy mottle, which an asymmetrical discoloration of *Citrus* leaves that is commonly mistaken as a sign of nutrient deficiency. A *Citrus* greening infected orange tree displays a sparseness of the canopy that reveals much of the set fruit and provides a line of sight to the scaffold limbs and trunk. An additional common symptom of a *Citrus* greening infected tree is dieback at the peripheries where many of the fruit bearing limbs have lost their leaves.

The new cultivar was asexually reproduced at Rolling Meadow Ranch Groves LLC'a *Citrus* nursery in Lake Wales, Fla., by inverted "T" bud-grafting onto US-942 rootstock on Feb. 9, 2020. It was grafted one day after the *Valencia* control, which was also on US-942. The new cultivar had a uniform bud break and maintained its vigor after being replicated. The new cultivar rapidly outgrew the *Valencia* control trees and maintained its unique leaf structure after asexual reproduction. The leaves of the new cultivar were more than double the size of the leaves of the *Valencia* control trees. The leaves of the new cultivar contained significantly more stomata on the adaxial and abaxial leaf surfaces so that the new cultivar was able to transpire at a higher rate, increasing the rate of photosynthesis.

The new cultivar was ready to be planted in the field months before the *Valencia* control trees and all other varieties that were grafted at the same time, which included W-Murcott, Early gold, and Vernia. This is astounding because the new cultivar was grafted with *Citrus* greening infected budwood, while the control trees were grafted with certified disease free budwood. The new cultivar showed blotchy mottling on its leaves, indicating that the *Citrus* greening infection persisted through the budding process, but the new cultivar was able to outgrow any negative effects of *Citrus* greening and was the first to be transplanted to the grove. There has not been a sweet orange variety to date that has shown this level of resiliency to *Citrus* greening. One hundred thirty-eight of the asexually reproduced trees were planted on Rolling Meadow Ranch Groves LLC's property in Lake Wales, Fla. on Sep. 15, 2020 for field evaluation. The genetics have remained stable in this generation and all planted trees have maintained the same growth habits and foliar characteristics of the parent tree. Trees are 3-5 times larger than all varieties planted around the same time. A notable characteristic of the one-year old trees is that they are thornless. Typically, juvenile *Citrus* trees are thorny, especially those with high vigor. The asexually reproduced trees have yet to have a reproductive flush, but this will likely occur in the spring of 2022.

SUMMARY

The present invention is a new cultivar of *Citrus Sinensis* named 'Noah' that has a resistance or tolerance to *Citrus* greening.

The new cultivar possesses a dense canopy that grows vigorously and conceals much of the set fruit. 'Noah' differs from its antecedent and all other known *Citrus* varieties such as the *Citrus reticulata*, 'UF1351' (U.S. Plant Pat. No. 31,290), that exhibit some *Citrus* greening resistance. The new cultivar exhibits atypical growth behavior where the branches often double back and grow in a disorderly fashion in contrast to the growth habit of 'UF1351'. This occurs because the new cultivar is extremely vigorous, while still setting a substantial amount of fruit. This is not common with known *Citrus sinesis* or 'UF1351' as usually vigorous vegetative growth is accompanied by a decrease in fruit set. New branches of the new cultivar are abnormally long, bearing large fruit loads, causing them to bend. The bent branches enlarge and harden before the fruit can be harvested, leaving them permanently distorted. However, this is not an impediment to the new cultivar but us merely a distinct characteristic when compared to 'UF1351', for example.

The sport limb growth is vigorous and can outpace the rootstock in caliper size. This may become an issue as the new cultivar ages, and a more vigorous rootstock may need to be selected to keep pace with growth of the new cultivar.

The fruit on the new cultivar is of higher quality and larger size than what is produced on *Citrus* greening infected orange trees. The new cultivar has a longer harvesting window compared to current orange trees and the color break is delayed. The delay in color break is due in part to the fruit being shaded by the vigorous growth of the new cultivar. The extended harvesting window is a result of the new cultivar being substantially healthier. Maturity testing showed that the harvesting of the new cultivar may begin at the same time as the *Valencia* orange trees (unpatented). The fruit of the new cultivar is seedless and sometimes possesses a secondary fruiting body like that on a navel orange, but the navel of the new cultivar is typically smaller in size. The fruit shape of the new cultivar is very rounded and large, with a slightly thicker peel when compared to the *Valencia* orange trees. Generally, the fruit size and shape are uniform throughout the new cultivar. The leaf structure of the new cultivar is noticeably different than current varieties of orange trees such as the *Valencia* orange tree and 'UF1351'. The leaves of 'Noah' are substantially larger that current orange trees and have a distinct waviness on the leaf edges and can be readily and unambiguously distinguished when compared to its antecedent or 'UF1351'.

BRIEF DESCRIPTION OF THE DRAWINGS

The accompanying colored photographs illustrate the overall appearance of the new cultivar of *Citrus Sinensis*, showing the colors as true as it is reasonably possible to obtain in colored reproductions of this type. Colors in the photographs differ slightly from the color values cited in the detailed botanical description, which accurately describes the colors of the new cultivar of *Citrus Sinensis*.

DETAILED BOTANICAL DESCRIPTION

Figure 1:
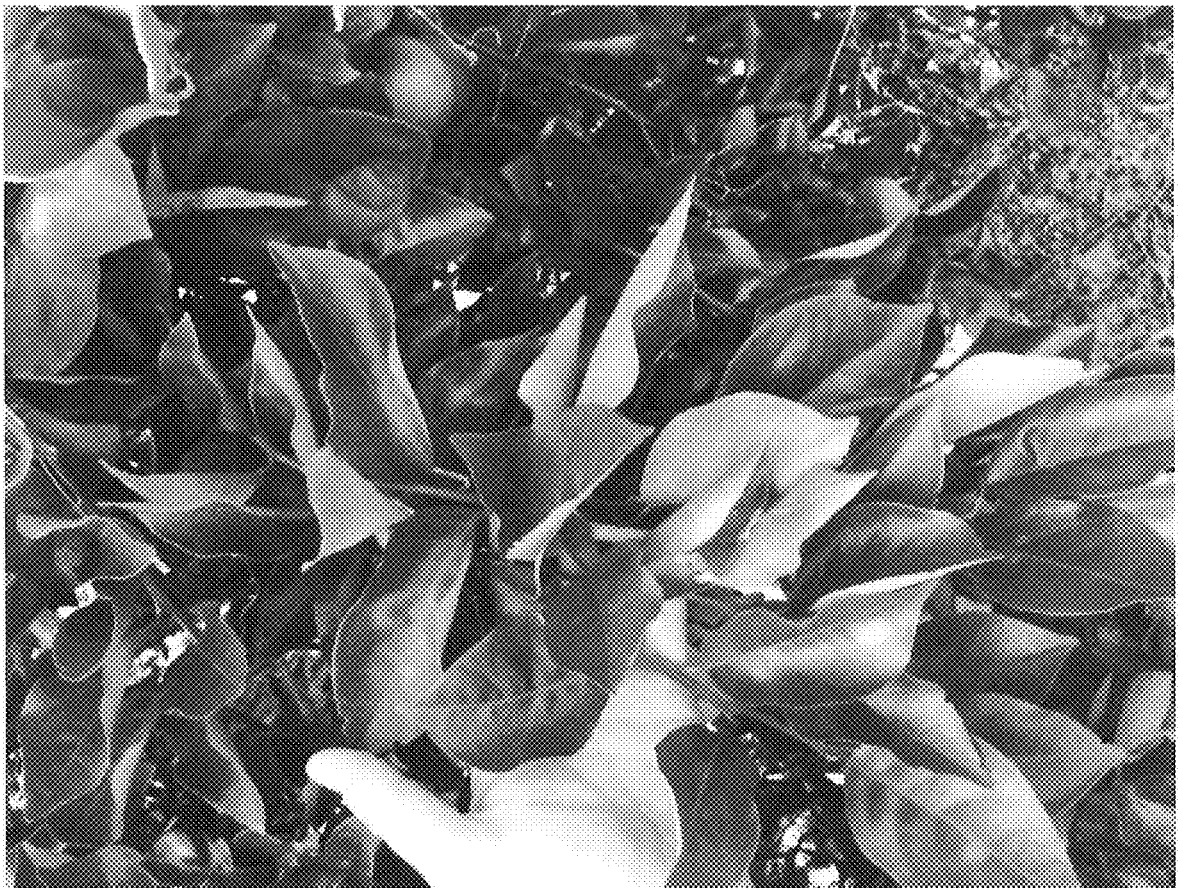
FIG. 1 shows the new cultivar possessing blotchy mottled leaves, indicating that it is infected with *Citrus* greening and although it is infected, the new cultivar shows nearly no other signs of infection or decline.
Figure 2:
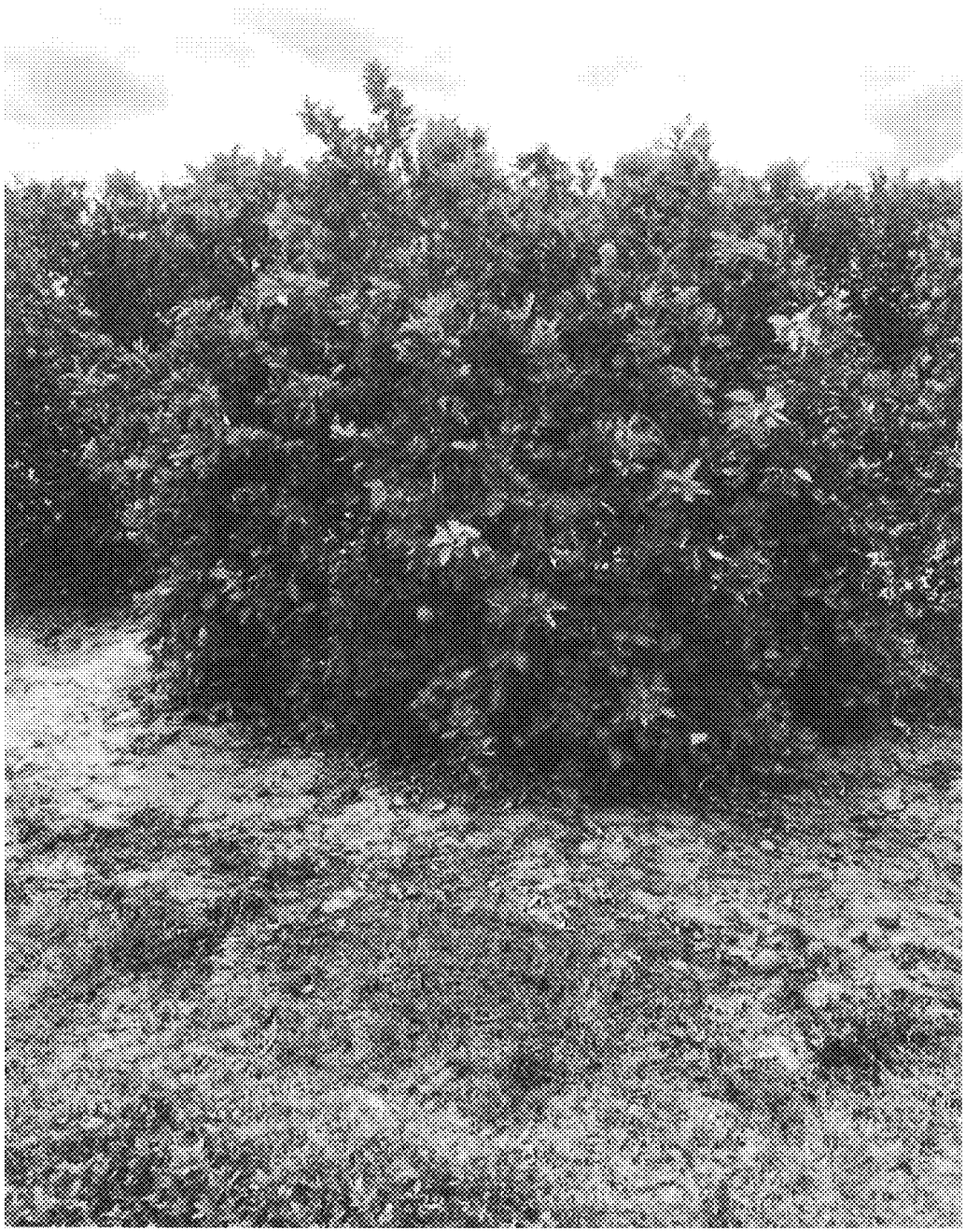
FIG. 2 shows the new cultivar possesses a dense canopy that grows so vigorously that it conceals much of the set fruit.
Figure 3:
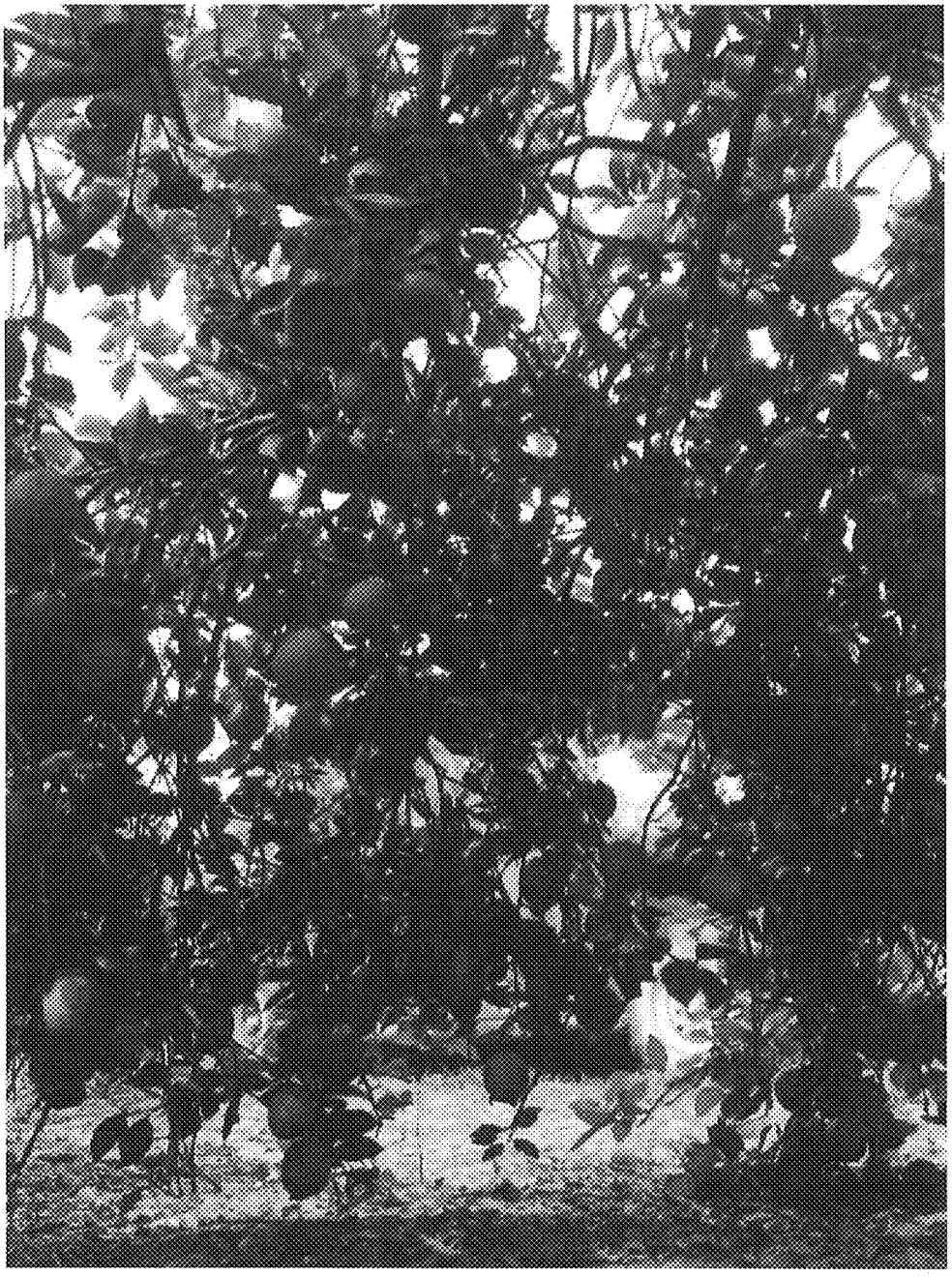
FIG. 3 shows a significant fruit load of the new cultivar.
Figure 4:
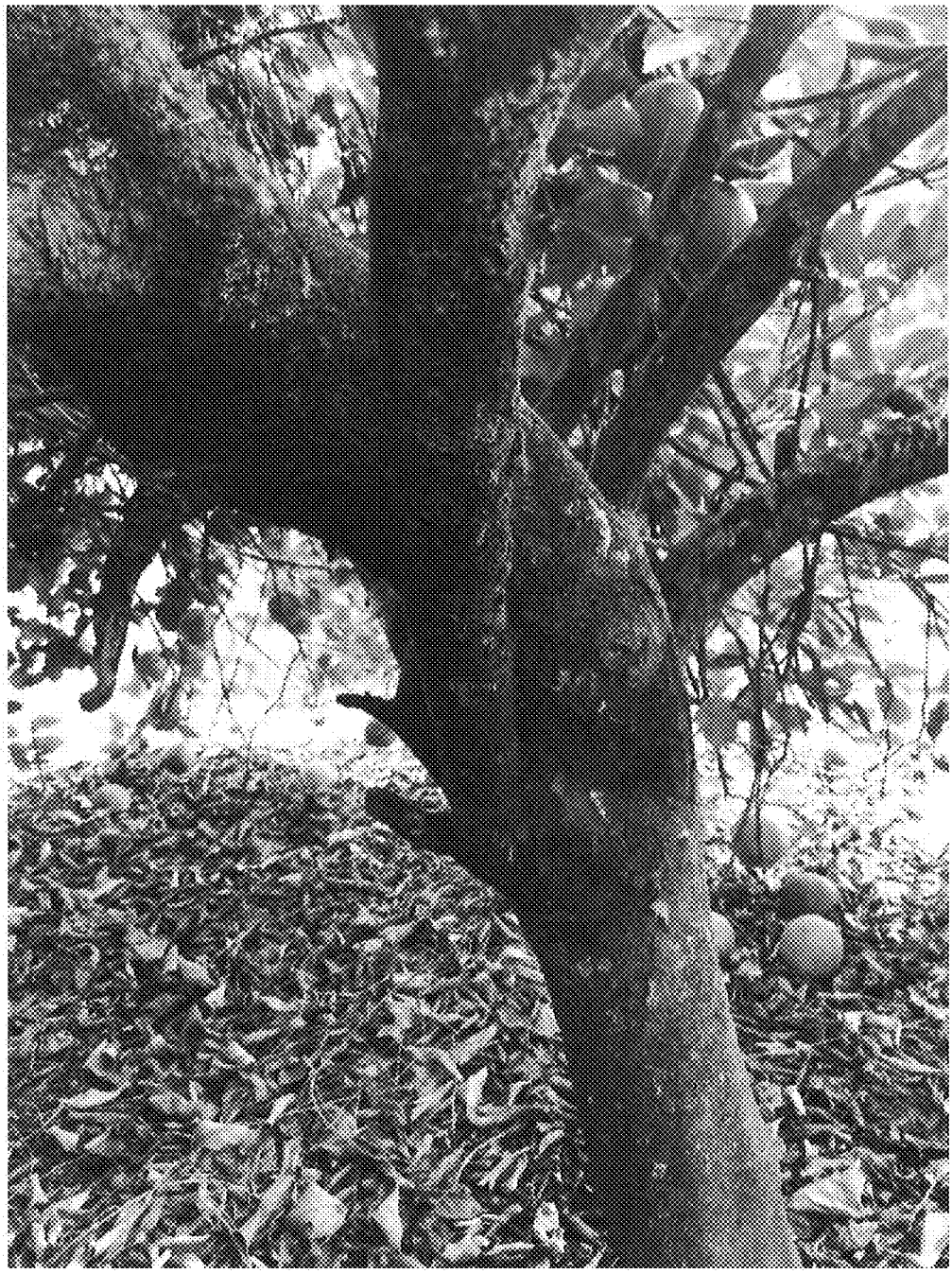
FIG. 4 shows where a sport limb of the new cultivar began and how it has dominated the growth coming out of the trunk.
Figure 5:
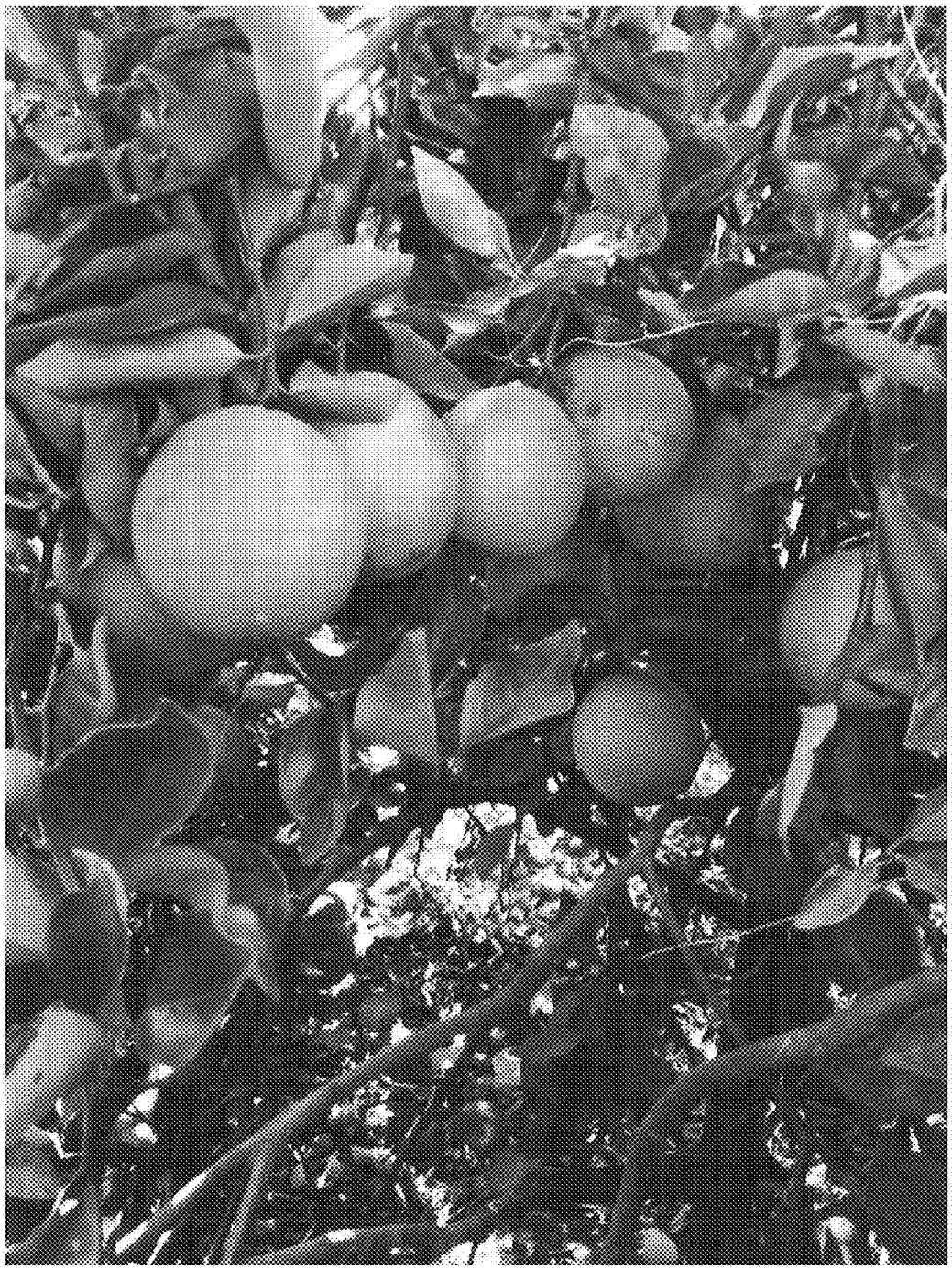
FIG. 5 shows that the fruit of the new cultivar sets in clusters and hangs from unusually long branches.
Figure 6:
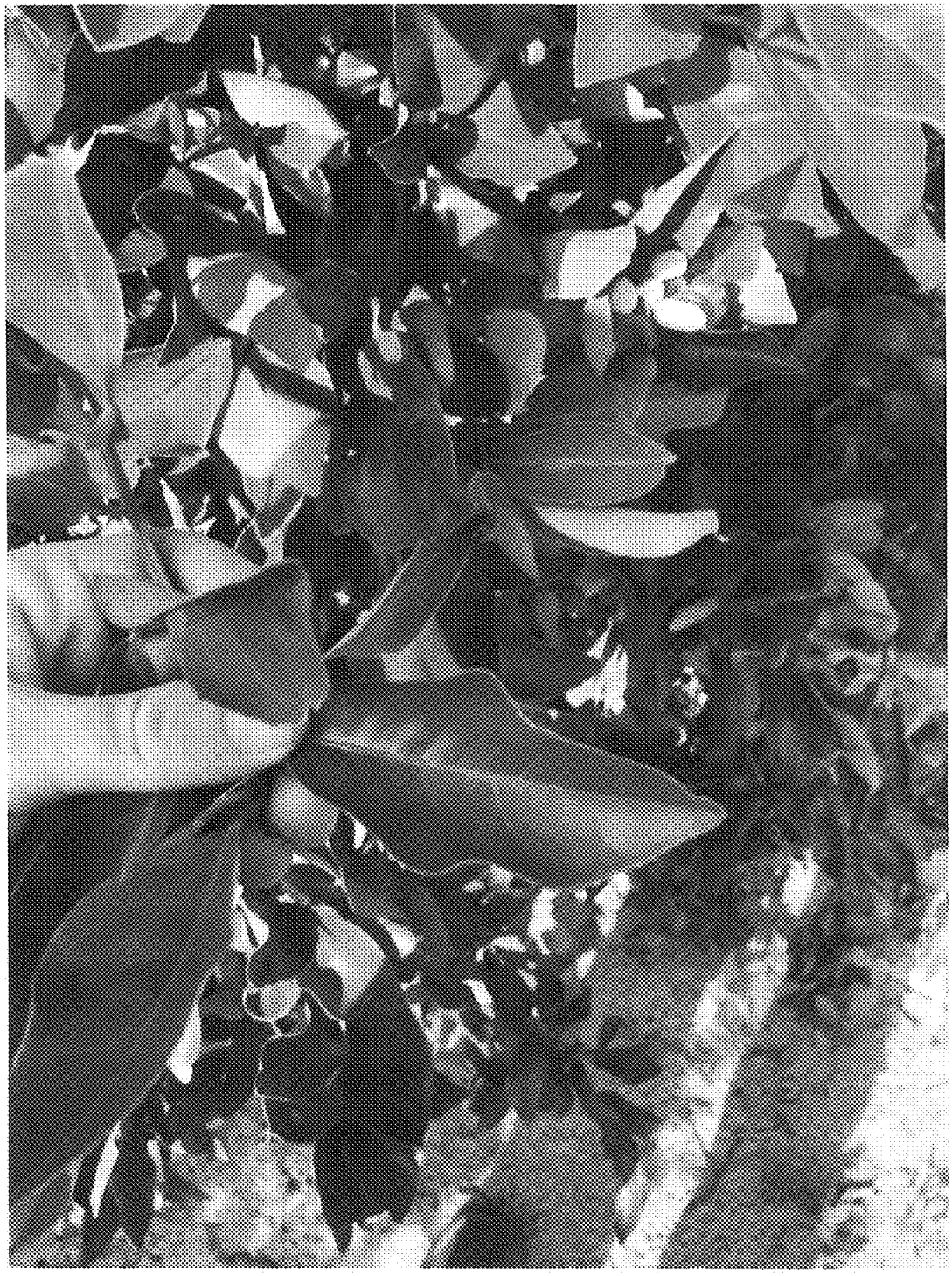
FIG. 6 shows the leaves of the new cultivar are substantially larger with a distinct waviness on the leaf edges.
Figure 7:
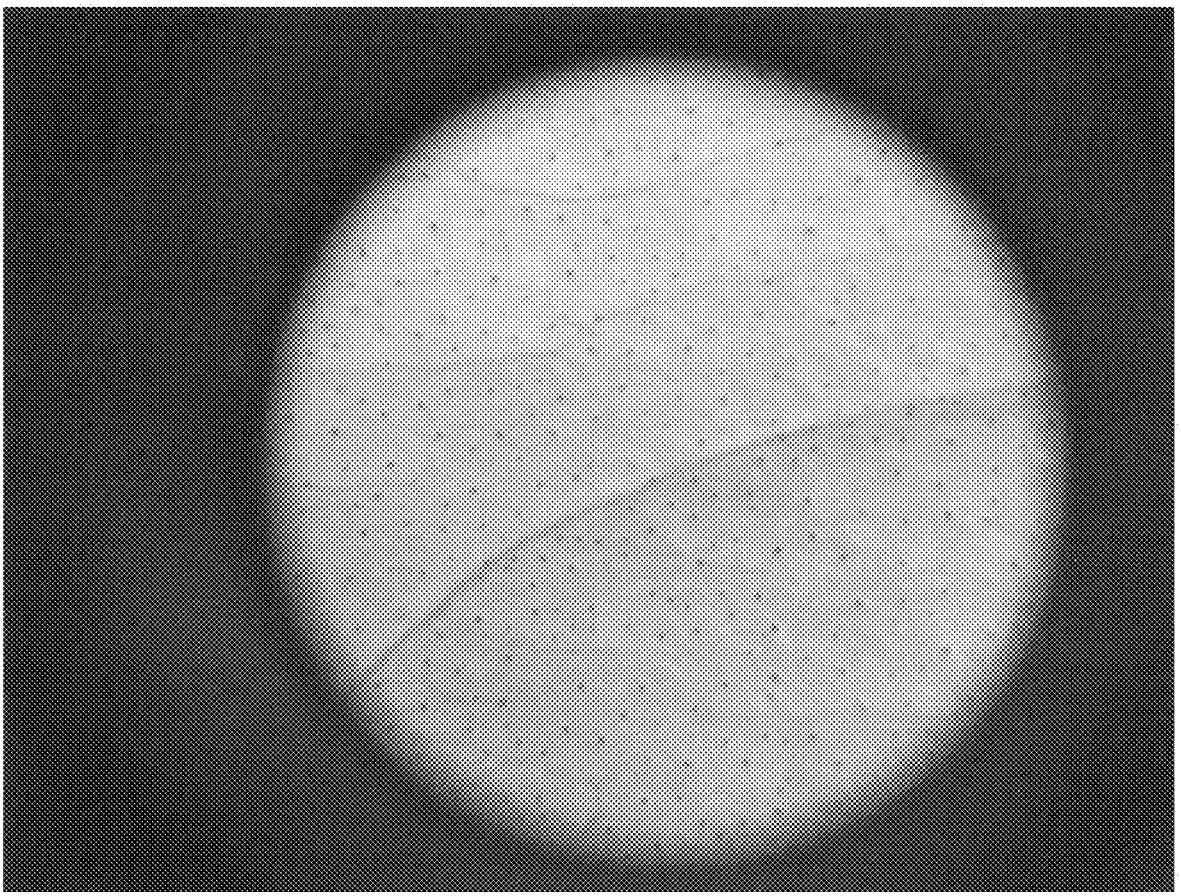
FIG. 7 shows under magnification the leaves of the new cultivar contain significantly more stomata on the abaxial leaf surfaces.

In the following description, color references are made to The Royal Horticultural Society Colour Chart, 2001 except where general terms of ordinary dictionary significance are used.

Tree description:

*Botanical.*—*Citrus sinensis.*
*Common name.*—Sweet orange.
*Parentage.*—Sport limb from '*Valencia*' (unpatented) tree.
*Tree size.*—Medium to large for 9-year-old tree.
*Height.*—2.74 m.
*Tree spread.*—4.21 m (in row). 3.96 m (across row).
*Vigor.*—Strongly vigorous.
*Density.*—Very dense outer canopy.
*Crown.*—Compact/Dense.
*Form.*—Oblate, slightly weeping.
*Growth habit.*—Tree as weak apical dominance which causes extensive branching. Typical branch lengths are 30-82 cm. Terminal ends of shoots produce 3-7 new sprouts with equal vigor. When the sprouts elongate and mature, the cumulative weight of the sprouts force the branch to bend downward increasing branch angles, sometimes in excess of 90 degrees. As a result, the growth habit is more out and down rather than vertical, giving the tree a weeping appearance. The extensive branching creates a dome-like structure where the interior of the canopy is heavily shaded and absent of leaves, twigs, and fruit.
*Twig vestiture.*—Glabrous.
*Twig coloration* (*2nd year*).—Striate. RHS 199B.
*Thorns.*—Absent.
*Prickles.*—Absent.
*Bark color.*—RHS 199A (greyed-brown).
*Trunk diameter.*—15.24 cm, taken 15 cm above graft union.
*Branch frequency.*—High.
*Branch strength.*—Strong.
*Limb diameter.*—7-10 cm.
*Stem strength.*—Strong and flexible, not brittle.
*Ploidy number.*—Diploid.

Leaf description:

*Arrangement.*—Alternately.
*Type.*—Simple.
*Margins.*—Crenate.
*Blades.*—Medium conduplicate. Undulated in the plane perpendicular to the lamina oriented along the midrib, with a wave-height of 12 mm.
*Apex.*—Cuspidate.
*Base.*—Rounded.
*Size* (*lamina average*).—Length: 9.37 cm. Width: 5.78 cm. L/W ratio: 1.62.

*Thickness*.—0.39 mm.
*Color adaxial*.—RHS 134A.
*Color abaxial*.—RHS 144A.
*Texture*.—Smooth, Glabrous (both sides).
*Petiole vestiture*.—Glabrous.
*Petiole wings*.—Brevipetiolate. Cuneate.
*Width and length of petioie wings*.—Length 1.6 cm, width 0.48 cm.
*Petiole length*.—1.62 mm.
*Petiole wing*.—Leaflet Blade Junction: Wing adjoining Blade.
*Petiole color*.—RHS 134A.

Flower description:
*Flower fragrance*.—Typical sweet orange.
*Date of first bloom*.—Late February to early March (central Florida).
*Calyx size*.—9 mm.
*Calyx color*.—RHS 137A (green).
*Petals*.—Quantity per flower: 5.
*Petals color*.—White upon abscission.
*Length and width of the petals*.—Length 1.95 cm; width 8 mm.

Reproductive organs:
*Fertility*.—Self fertile.
*Stamen number*.—4 per petal.
*Length of the stamens*.—1.3 cm.
*Anther color*.—RHS 3A (yellow).
*Anther shape*.—Globular.
*Anther length*.—Approximately 0.2 cm.
*Pollen*.—RHS 9C (yellow).
*The relative amount of viable pollen*.—Moderate.
*Style length*.—Approximately 0.5 cm.
*Style color*.—RHS 1D (green yellow).

Fruit description:
*Time of maturity*.—Mid to late February in central Florida.
*Time of first picking*.—Late February.
*Time of last picking*.—Mid June.
*Size*.—Uniform.
*Shape*.—Spherical to slightly prolate.
*Apex*.—Rounded.
*Base*.—Rounded to weakly truncated.
*Height* (*average*).—82 mm.
*Width* (*average*).—78 mm.
*Fruit skin color*.—RHS 23A (yellow orange).
*Fruit flesh color*.—RHS N25B (orange).
*Mesocarp color*.—RHS 18D (yellow orange).
*Segments* (*average*).—11.
*Naval*.—Present on approximately 60% of fruit.
*Skin texture*.—Medium rough, similar to "*Valencia*" (unpatented).
*Radial groove*.—None.
*Seed*.—Seedless (0-2 seeds per fruit).
*Fruit flavor*.—Sweet and tart.
*Juice data*.—Has a maturity date similar to a "*Valencia*" (unpatented), with a longer harvesting window. Similar juice color and slightly higher brix and brix acid ratio than that of *Valencia* oranges in the same block. Juice test from Feb. 13, 2090: Brix: 10.50. Acid: 0.84. Ratio: 12.5. All juice data is from greening infected trees.
*Presence or absence of fruit clustering* (*infructescence*).—Present.
*Position of the broadest part of the fruit* (*towards the stalk end, at the middle, or towards the distal end*).—Middle.
*The presence or absence of a fruit neck*.—Not present.
*The length and thickness of any fruit neck, or if no fruit neck exists*.—Not present.
*The presence or absence of a depression at the stalk end*.—Present.
*The depth of any such depression*.—Shallow.
*The absence or presence of any constriction at the stalk end*.—Absent.
*How strongly any stalk end constriction is expressed on a relative basis*.—N/a.
*A description of any depression at stalk attachment for necked varieties*.—N/a.
*The presence or absence of a fruit collar*.—Absent.
*The height and diameter of any fruit collar*.—N/a.
*A description of the abscission layer between the floral disc and the fruit*.—The floral disc or calyx tightly adheres to the fruit. When calyx is removed there is a cylindrical depression 5 mm wide and 2 mm deep.
*The general shape of the distal part excluding the nipple*.—Rounded to weakly truncated (flat).
*Bulging of navel, and depression at the distal end* (*flattened slightly rounded strongly rounded*).—Weak bulging.
*The presence or absence of any depression at the distal end*.—Present on pieces without navel.
*The depth and diameter of any distal end depression*.—3.7 mm wide and 0.81 mm deep.
*The presence or absence of any areola*.—Absent.
*The completeness of any areola*.—None.
*The type of any areola* (*smooth, grooved, ridged*).—None.
*The diameter of any areola*.—None.
*The diameter of the stylar scar*.—1.9 mm.
*The persistence of the style*.—None.
*The presence of any navel opening*.—Variable presence.
*The diameter of any navel opening*.—Variable, 12 mm or less.
*The relative sizes of fruit oil glands* (*all more or less the same size, larger ones interspersed by smaller ones*).—Larger ones interspersed by smaller ones.
*The sizes of fruit oil glands and a description as to how conspicuous they are*.—Moderate conspicuousness.
*The presence or absence of pitting and pebbling on fruit oil glands*.—Pitting and pebbling present.
*The density of any pitting on fruit oil glands*.—Sparse pitting.
*The degree of any pebbling on fruit oil glands*.—Peddling moderate.
*The fruit rind thickness and adherence to flesh*.—Medium thickness 6 mm.
*Fruit rind strength and oiliness*.—High strength and moderate oil.
*The conspicuousness of oil glands on the inner surface of the fruit rind*.—Not conspicuous.
*The relative density or the albedo* (*loose, medium, dense*).—Dense.
*The relative amount of albedo adhering to the flesh excluding strands*.—Moderate albedo adheres to the outer segment walls upon peeling.
*The presence or absence of albedo strands*.—Present.

*The relative amount of any albedo strands*.—One or two albedo strands may remain on each segment.

*A description of the core*.—Core is filled with albedo strands.

*Diameter of the core*.—10 mm.

*The absence or relative presence of rudimentary segments*.—Present.

*The coherence of adjacent fruit segment walls*.—Intermediate.

*The relative strength of fruit segment walls*.—Moderate.

*The length and thickness of juice vesicles*.—10 mm length and 2 mm thickness.

*The relative conspicuousness and coherence of juice vesicles*.—Conspicuous with strong coherence.

That which is claimed is:

1. A new and distinct cultivar of *Citrus Sinensis* plant named "Noah" as herein illustrated and described.

* * * * *